United States Patent [19]

Raines

[11] Patent Number: 5,228,646
[45] Date of Patent: Jul. 20, 1993

[54] LATCHING TRUMPET VALVE FOR MEDICAL INFUSIONS

[76] Inventor: Kenneth Raines, 1760 Easthill Dr., Bethlehem, Pa. 18018

[21] Appl. No.: 908,418

[22] Filed: Jul. 6, 1992

[51] Int. Cl.$^5$ .................. F16K 3/24; F16K 31/44; F16K 35/00
[52] U.S. Cl. .................... 251/95; 251/322; 251/323; 251/324
[58] Field of Search .............. 251/95, 110, 215, 321, 251/322, 323, 324, 336, 342, 343, 347, 348, 297

[56] References Cited

U.S. PATENT DOCUMENTS

| | | | |
|---|---|---|---|
| 1,301,577 | 4/1919 | La Valley | 251/66 |
| 1,463,735 | 7/1923 | Varrieur | 251/100 |
| 2,506,722 | 5/1950 | Kuehn et al. | 251/322 |
| 2,591,514 | 4/1952 | Courtot | 251/297 |
| 2,678,147 | 5/1954 | Abplanalp | 251/342 |
| 2,690,895 | 10/1954 | Barcus | 251/297 |
| 2,723,829 | 11/1955 | Anderson | 251/100 |
| 2,986,370 | 5/1961 | Girton | 251/100 |
| 3,146,987 | 9/1964 | Krayl | 251/100 |
| 3,169,672 | 2/1965 | Soffer et al. | 251/95 |
| 3,220,695 | 11/1965 | Downey et al. | 251/263 |
| 3,305,144 | 2/1967 | Beres et al. | 251/95 |
| 3,370,143 | 2/1968 | Barney | 200/166 |
| 3,434,694 | 3/1969 | Skinner | 251/215 |
| 3,788,602 | 1/1974 | Kitzie | 251/312 |
| 3,940,106 | 2/1976 | Hart et al. | 251/100 |
| 4,147,184 | 4/1979 | Jess | 251/312 |
| 4,573,658 | 3/1986 | Gordon et al. | 251/95 |
| 4,691,895 | 9/1987 | Garff | 251/292 |
| 5,064,168 | 11/1991 | Raines et al. | 251/323 |
| 5,083,743 | 1/1992 | Gordon et al. | 251/95 |
| 5,085,135 | 2/1992 | Collignon | 251/95 |

Primary Examiner—George L. Walton
Attorney, Agent, or Firm—Shoemaker and Mattare Ltd.

[57] ABSTRACT

A valve for controlling medical infusions includes a one-piece plastic body, and a plunger assembly inserted into the body from one end. The plungers is connected to a manually operable cap containing a return spring, and the cap has a rim with a pair of internal barbs which engage an external flange on the body when the cap is fully depressed, to latch the valve open. A pair of flats on the cap rim are squeezed together in order to release the latch.

6 Claims, 2 Drawing Sheets

LATCHING TRUMPET VALVE FOR MEDICAL INFUSIONS

BACKGROUND OF THE INVENTION

This invention relates generally to valves, and more particularly to a valve having a spool-type valve member driven by a linear, spring biased actuator including a cap which releasably latches the valve in its open position.

There is a need for a valve which, while attached to a surgical instrument such as an irrigation/aspiration probe, can be operated with one hand. Ergonomically, it is desirable for a valve to be mounted at right angles to a probe, and to attach to a standard medical luer taper.

It is also desirable to avoid placing a return spring within the fluid flowpath, and to provide a design that permits in-line vertical assembly of components without gluing or welding, to facilitate high volume, low cost production.

A valve satisfying the above requirements is disclosed in U.S. Pat. No. 5,064,168, which is incorporated herein by reference. In that valve, a spool-shaped head is moved from a closed position to an open position by depressing a cap against the force of a spring within the cap. When the cap is released, the valve closes automatically. In some applications, however, it would be desirable to be able to lock or latch the valve in an open position. There are a number of prior valves, particularly faucet valves, having a latch-open feature. Prior approaches tend to be too bulky, complicated, or costly to be suitable for use in a small, inexpensive medical infusion valve.

SUMMARY OF THE INVENTION

In view of the foregoing considerations, it is an object of the invention is to provide an inexpensive valve of simple manufacture and assembly, suitable for medical infusions, or other single-use applications.

Another object is to provide a spool-type valve with a latching actuator cap which can be released in a simple and intuitive manner using only one hand.

A valve embodying the invention includes a one-piece plastic body, and a plunger assembly inserted into the body from one end. The body includes a central cylindrical portion, a tubular lateral outlet, and a tubular lateral inlet extending perpendicular to the central portion, and above the outlet. An uninterrupted 360° band of the central bore form a seat between the outlet and the inlet. The plunger assembly includes a resilient, circumferential lip that engages the seat in the closed position of the valve, and a circumferential recess adjacent the lip, that permits fluid to flow through the valve in its open position.

The plunger is moved by depressing a cap containing a compression spring, which normally keeps the valve closed. The cap has a cylindrical rim with a pair of internal barbs that, when the cap is fully depressed, latch behind a chamfered outer flange at the top of the valve body. The cap is released from its latched position by squeezing a pair of opposed flats on the rim, which disengages the latching barbs.

An advantage of the invention is that it provides sure on-off performance, required for safety purposes in medical fluid administration procedures. Another advantage is that it can be used by medical personnel to control fluid flow in operations demanding one hand operation.

BRIEF DESCRIPTION OF THE DRAWINGS

In the accompanying drawings.

DESCRIPTION OF THE PREFERRED EMBODIMENT

Figure 1:
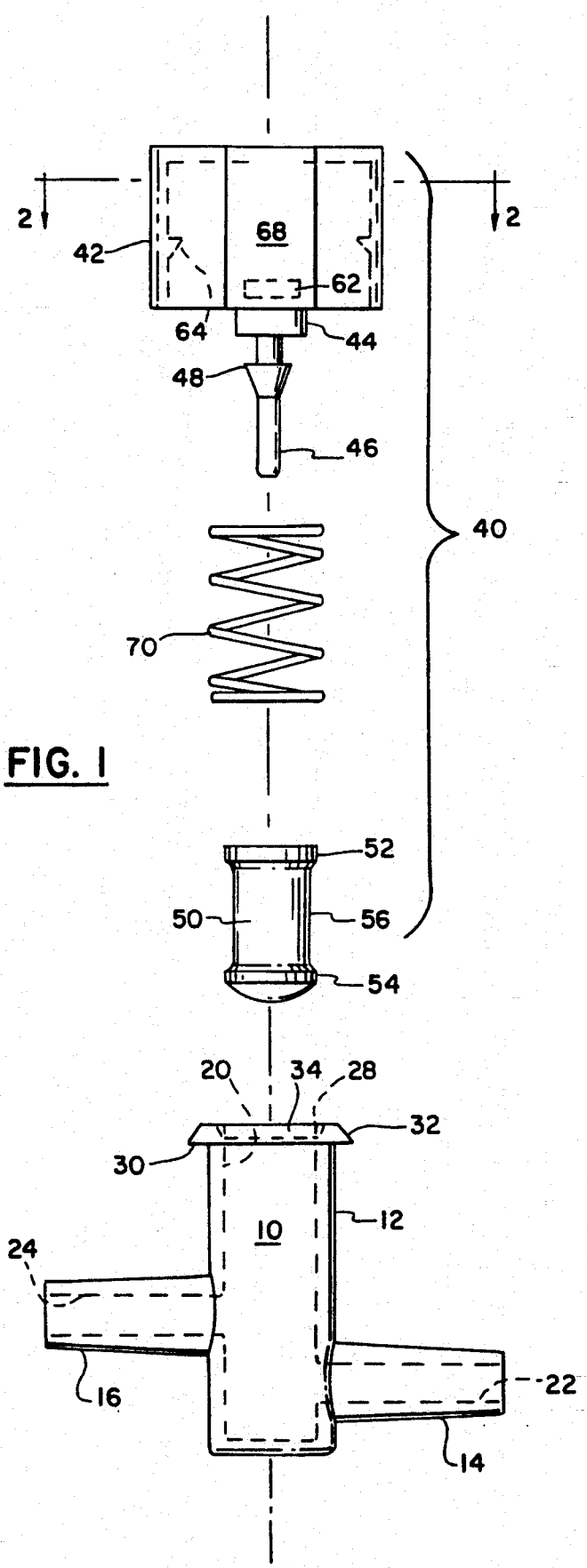
FIG. 1 is an exploded side elevation of a valve embodying the invention.
Figure 2:
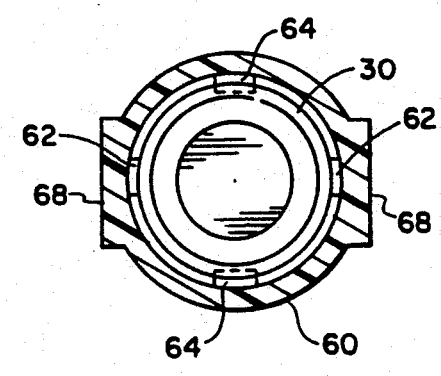
FIG. 2 is a sectional view thereof (with the spring and plunger omitted), taken on plane 2—2 in FIG. 1, showing the cap in its relaxed configuration.

As shown in FIG. 1, a valve embodying the invention comprises a molded plastic body 10 including a central portion 12, a tubular outlet 14 having an axis perpendicular to the central portion, and a tubular inlet 16 extending laterally from the central portion, on the side opposite the outlet, and above the level of the outlet. The inlet and outlet are externally tapered, while the intersecting bores 20, 22 and 24 of the elements 12, 14 and 16 are each cylindrical and smooth. The vertical distance or offset between the inlet and outlet is sufficiently large to leave an uninterrupted 360° band of the bore 20 between the bores 22 and 24.

The upper end of the bore 12 has an internal chamfer 28, to facilitate insertion of the plunger, and a circumferential outer flange 30, the upper edge of which is chamfered at 32. The inner chamfer 28 is slightly counterbored at 34.

The other major component of the valve is a plunger assembly, designated generally by the numeral 40, which comprises a hollow cap 42 molded integrally with a downwardly extending shaft 44 that terminates at a distal tip 46 having a circumferential barb 48. A resilient plunger 50 is pushed onto the barb, which retains the plunger on the tip. The plunger is spool-shaped, being mushroomed slightly at both ends, so that two lips 52 and 54, slightly larger in diameter than the bore 20, are defined on either side of a central cylindrical outer surface 56 of reduced diameter. The annular space 58 between the bore 20 and the surface 56 permits fluid to flow through the valve when the valve is in the position of FIG. 5, as suggested by the arrows.

Figure 4:
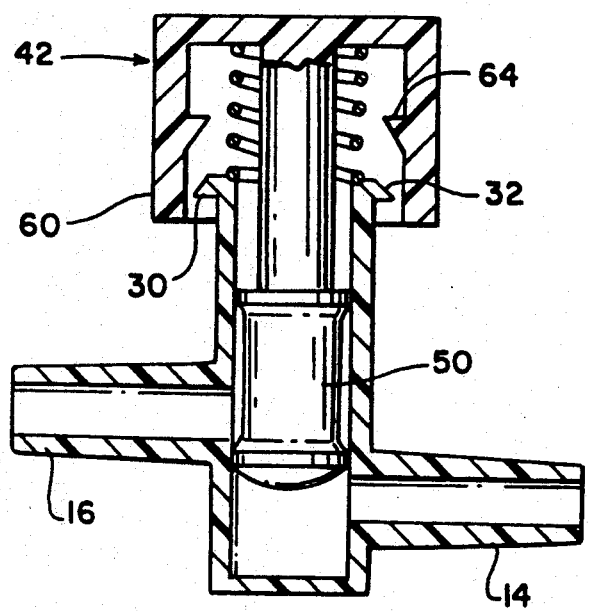
FIGS. 4 and 5 are side elevations, in partial section, showing the assembled valve in its closed and open positions, respectively.
Figure 5:
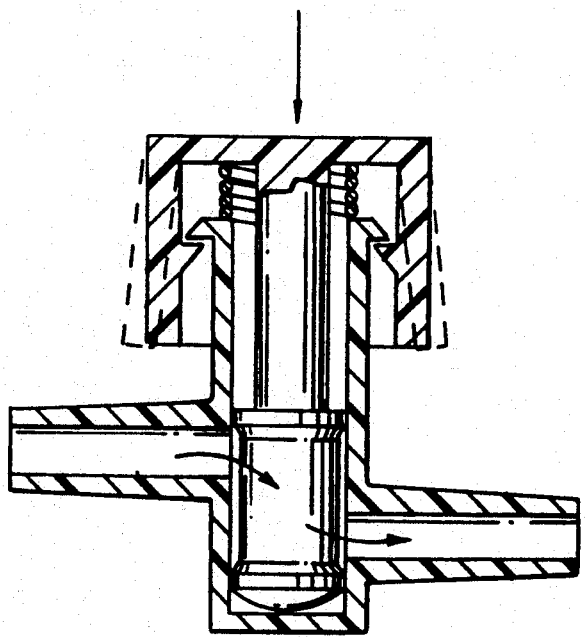

The cap 42 has a cylindrical rim 60, provided at its bottom edge with a pair of retention barbs 62, each of which is chamfered on the bottom (FIGS. 4-5). The function of these barbs is to prevent the cap and plunger from escaping from the assembly. The spacing of the barbs 62 is less than the outer diameter of the flange 30, so that once assembled, these barbs cooperate with the flange (see FIG. 4) to prevent or resist removal of the plunger assembly. The chamfer permits the cap to be forced over the body flange during assembly.

A second pair of internal barbs 64 are disposed higher up on the cap rim. These barbs, referred to as latching barbs, are provided to lock or latch the cap in its lowermost position, to hold the valve open. Like the barbs 62, these are chamfered on their lower edges, so that they can pass over the external flange on the valve body. Once engaged behind the flange (FIG. 5), the barbs cannot be released by pushing or pulling on the cap, or by rotating it. As a result, the cap resists accidental unlatching, as well as attempts to unlatch it by untrained people.

Figure 3:
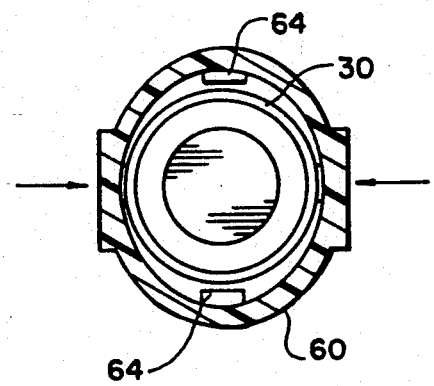
FIG. 3 is a view corresponding to FIG. 2, showing the cap in its deformed release configuration.

The cap has a pair of opposed flats 68, appearing in FIG. 1, on the exterior of its rim, which are aligned with the retention barbs 62 on an axis perpendicular to that of the latching barbs 64. By squeezing the flats together, the cap is deformed into the shape of an ellipse (see FIGS. 3 and 5) whose major diameter is sufficiently greater than that of the flange to release the retention barbs. The flats provide naturally attractive spots to apply squeezing pressure, and thus are somewhat intuitive. Furthermore, they stiffen the rim locally, so that it is not so easy to release the retention barbs by squeezing the cap between the flats.

The cap, particularly the rim, is constructed and dimensioned, considering the cap material, so as to provide sufficient resilience to enable one to release the latch easily, yet sufficient stiffness to prevent accidental unlatching. In a preferred cap, constructed from a moldable plastic, and intended for use with a valve body having an outer diameter of about 0.31 inch, the rim is 0.36 inch long, has an external diameter of 0.475 inch, and a wall thickness of 0.045 inch. To scale the cap up or down, and to achieve a desired resiliency, should be a matter of ordinary skill.

A stainless steel compression coil return spring 70 is disposed around the shaft 44 of the plunger, and abuts the bottom of the top surface of the cap, and the counterbore 34 of the body portion, which centers it around the shaft.

The rest position of the valve is shown in FIG. 4, wherein the spring holds the plunger in its extreme upward position defined by the flange 30 and lower barbs 62. The parts are dimensioned so that 360° of the lower lip of the plunger at this point is in contact with the seat in the valve bore, providing a fluid-tight seal.

The valve is opened by depressing the plunger to the open position (FIG. 5) determined by interference between the plunger and the shoulder 26, whereupon fluid can enter and pass through the annular space 58 around the plunger, from the outlet to the inlet. In the open position, the upper barbs 64 are engaged beneath the flange 30, and hold the valve open until the barbs 64 are released by squeezing the cap (FIG. 3) to deform the cap and thus release the barbs 64. The deformation of the cap is also illustrated by broken lines in FIG. 5.

Dimensions of the valve can be varied for various applications. In the presently contemplated medical application, the valve is sized to pass 100 ml per minute of 23° C. water at a head differential of one meter, and the valve is designed not to leak under inlet and outlet pressures of up to 45 psi. The material used for the body and plunger are USP Class VI approved for biocompatability.

The portions 16 and 18 are designated "outlet" and "inlet" above, but the flow direction could be reversed, if desired, for certain applications, and in fact, bidirectional flow is contemplated. These designations, when used in the claims that follow, are not intended to limit the invention to a particular use; they are used only for convenience and clarity. Similarly, use of the terms "top" or the like, is not intended to limit use of the invention to a particular orientation.

Additionally, the invention may be utilized in a variety of different valves, specifically including that shown in U.S. Pat. No. 5,064,168, whose disclosure is incorporated into this document.

In the preferred form of the invention, the flats are placed on an axis perpendicular to the axis of the upper barbs 64, since this arrangement produces the greatest deformation at the barbs; however, it would be possible to have some other angle between the axes; hence the term "misaligned" is used in the claims that follow.

Inasmuch as the invention is subject to modifications and variations, it is intended that the foregoing description and the accompanying drawings shall be interpreted as illustrative of only one form of the invention, whose scope is to be measured by the following claims.

I claim:

1. In a valve comprising a hollow body having a bore therein and a pair of fluid ports communicating with the bore, a plunger slidably disposed within the bore for movement between a closed position prohibiting fluid flow between said ports, and an open position permitting flow between said ports, a return spring for biasing said plunger toward one of said positions, and a manual operator extending from one end of the body for moving said plunger against said spring bias, the improvement wherein said body has an external continuous flange around said one end and said operator comprises a depressible cap having a rim extending over and outside said flange, said rim having a pair of opposed, internal latching barbs which engage behind said flange when the cap is fully depressed, said cap being sufficiently resilient that the latching barbs can be released by squeezing the rim at opposed spots misaligned with said latching barbs.

2. The invention of claim 1, further comprising a pair of opposed external flats on said rim, said flats lying on an axis substantially perpendicular to an axis extending through said latching barbs, whereby one can release the valve from its latched position by squeezing the flats toward one another.

3. The invention of claim 2, further comprising a pair of opposed retention barbs extending inwardly from said rim, and lying on an axis substantially parallel to that of said flats, said retention barbs engaging said flange, to prevent removal of said plunger from said body, when the valve is in its closed position.

4. The invention of claim 3, wherein the flange has a chamfered leading edge, to facilitate assembly of the valve.

5. The invention of claim 3, wherein each of said retention barbs has a chamfered leading edge, to facilitate assembly of the valve.

6. The invention of claim 1, wherein each of said latching barbs has a chamfered leading edge, to facilitate moving the cap to its latched position.

* * * * *